United States Patent [19]

Marrs et al.

[11] Patent Number: 4,975,113
[45] Date of Patent: Dec. 4, 1990

[54] HERBEICIDAL COMPOSITION

[75] Inventors: Gordon J. Marrs, Maidenhead; David J. Brown, Camberley, both of England; Roger P. Heath, Victoria, Australia

[73] Assignee: Imperial Chemical Industries PLC, London, England

[21] Appl. No.: 108,324

[22] Filed: Oct. 14, 1987

[30] Foreign Application Priority Data

Oct. 14, 1986 [GB] United Kingdom ............... 8624644

[51] Int. Cl.$^5$ ............................................. A01N 33/24
[52] U.S. Cl. ............................................. 71/121; 71/98; 71/103; 71/105; 71/106; 71/118; 71/DIG. 4
[58] Field of Search ......................... 71/121, DIG. 1

[56] References Cited

U.S. PATENT DOCUMENTS

| | | | |
|---|---|---|---|
| 4,564,381 | 1/1986 | Bieringer et al. | 71/88 |
| 4,666,510 | 5/1987 | Watson et al. | 71/121 |
| 4,699,727 | 10/1987 | Dexheimer | 252/77 |
| 4,711,730 | 12/1987 | Gosselink et al. | 252/174.23 |

FOREIGN PATENT DOCUMENTS 0102003  3/1984  European Pat. Off. .......... 71/111
1170357  11/1969  United Kingdom .
1531843  11/1978  United Kingdom .
2077732  12/1981  United Kingdom .
2110673   6/1983  United Kingdom .

Primary Examiner—Glennon H. Hollrah
Assistant Examiner—Susan P. Treanor
Attorney, Agent, or Firm—Cushman, Darby and Cushman

[57] ABSTRACT

A herbicidal composition comprising a herbicidal cyclohexane dione of partial structure (I):

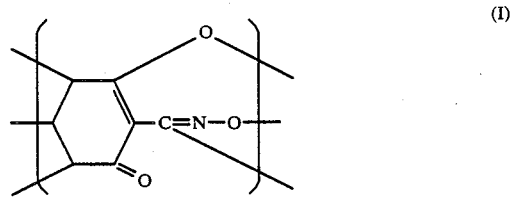

and a surfactant having terminal hydroxy groups in which the hydroxy groups have been replaced by organic blocking groups.

2 Claims, No Drawings

HERBEICIDAL COMPOSITION

This invention relates to a herbicidal composition containing as active ingredient a herbicidal compound of the cyclohexane dione class.

As used herein the expression "cyclohexane dione" includes herbicidal compounds having a partial structure (I):

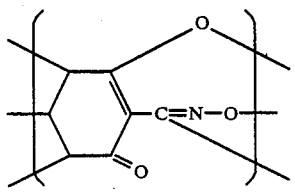
(I)

Many herbicidal compounds of this are known, for example from UK Pat. No 3,950,420, E-P-A Nos. 0080301, 00885529, Japanese Kokai Nos. 7795636 and 8175408, U.S. Pat. No. 4,440,566 and as described in the Proceedings of the Brighton Crop Protection Conference-Weeds (1), 93-8.

Particular compounds of this type include alloxydim, sethoxydim, cloproxydim, cycloxydim, and the compound of formulae:

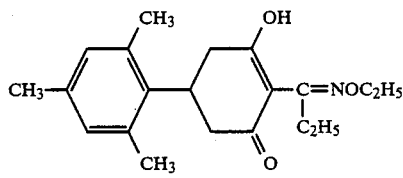

Compounds of this type have a tendency to be unstable particularly in the presence of water and when formulated into herbicidal compositions may decompose on standing. This clearly has an adverse effect on the shelf-life of products containing such compounds.

Conventional surfactants used as emulsifiers, coemulsifiers and wetters in herbicidal compositions contain terminal hydroxy groups. These sufactants are typically polymeric compounds of general formula (II) or (III):

$$CH_3(CH_2)_xO(CH_2CH_2O)_yH \quad (II)$$

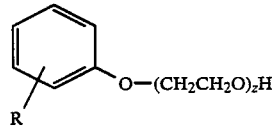
(III)

where R is an alkyl group, x is an integer of from 1 to 20 preferably from 8 to 17 and y and z are integers of from 1 to 100 preferably from 2 to 50.

Examples of alkyl groups R include those having up to 20 carbon atoms, for example from 8 to 12 carbon atoms.

The applicants have now found a formulation which gives improved stability for herbicidal compositions including cyclohexane diones as active ingredient.

According to the present invention there is Provided a herbicidal composition comprising a herbicidal cyclohexane dione, and a surfactant having terminal hydroxy groups which have been replaced by a blocking group.

The applicants have found that formulations in accordance with the Present invention have improved stability and will tolerate small amounts of water without significantly decreasing the stability.

Examples of surfactants include those of the nonionic type.

Nonionic surface active agents include: the condensation products of ethylene oxide with fatty acohols such as oleyl alcohol and cetyl alcohol; the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitin monolaurate, and their condensation products with ethylene oxide; ethylene oxide/propylene oxide block copolymers; and lauryl alcohol polyglycol ether acetal.

Suitable blocking groups for the terminal hydroxy $C_{1-20}$ alkyl ether, preferably $C_{1-6}$ alkyl ethers for example methyl or ethyl ether or carboxylic ester groups such as $C_{1-20}$ alkyl ester for example laurate esters or inorganic groups for example, halogen such as chlorine. Thus preferred examples of surfactants which may be employed in the formulations include compounds of formula (IV) and (V):

$$CH_3(CH_2)_xO(CH_2CH_2O)_{y-1}CH_2CH_2R^1 \quad (IV)$$

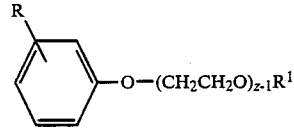
(V)

wherein R, x, y and z are as hereinbefore defined and $R^1$ is a halogen such as chlorine or a group $OR^2$ wherein $R^2$ is $C_{1-6}$ alkyl such are methyl or ethyl.

When $R^1$ is a group $OR^2$, compounds of formula (IV) and (V) can be prepared by reacting a compound of formula (II) or (III) respectively with an alkylating agent. Suitable alkylating agent include compounds of formula (VI):

$$R^2-Q \quad (VI)$$

wherein $R^2$ is as hereinbefore defined and Q is a leaving group such as halogen, for example methyl chloride. Additional examples of alkylating agents are dimethyl sulphate and dimethylcarbonate. Conventional reaction conditions can be employed in the process, described for example in Kirk-othmer, Encyclopaedia of Chemical Technology, 2nd Ed, Vol 1 pp. 882-901.

When $R^2$ is halogen, compounds of formula (IV) and (V) can be prepared by reacting compounds of formula (II) and (III) respectively with a halogenating agent such as thionyl chloride under conventional conditions.

The compositions may additionally contain an anionic surfactant, for example as a co-emulsifier. Suitable anionic surfactants include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acid, the di- and tri-isopropylnaphthalenesulfonic acids, the salts of the condensation Products of sulfonated naphthalene and naphthalene derivatives with formaldehyde, the salts of the condensation products of sulfonated naphthalene and naphthalene derivatives with phenol and formaldehyde, the salts of alkylarylbenzenesulfonic acids such as dodecylbenzene-sulfonic acid; the alkali metal, alkaline earth metal and ammonium salts of the long chain monoesters of sulfuric acid or alkylsulfates such as laurylsulfate and the mono esters of sulfuric acid with 5 fatty alcohol glycol ethers.

Particular preferred anionic surfactants for use in these compositions are dioctylsulphosuccinates as exemplified hereinafter.

Particularly preferred cyclohexane diones for use in the formulations are compounds of formula (VII)

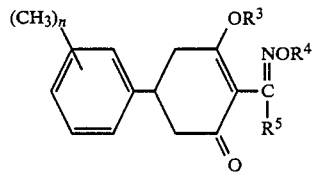

(VII)

where
R$^3$ is selected from the group consisting of: hydrogen; C$_1$ to C$_6$ alkyl; C$_2$ to C$_6$ alkenyl; C$_2$ to C$_6$ alkynyl; substittued C$_1$ to C$_6$ alkyl wherein the alkylg roup is substituted with a substituent selected from the group consisting of C$_1$ to C$_6$ alkoxy, C$_1$ to C$_6$ alkylthio, (C$_1$ to C$_6$ alkoxy)carbonyl, phenyl and substituted phenyl wherein the benzene ring is substituted with from one to three substituents selected from the group consisting of halogen, nitro, cyano, C$_1$ to C$_6$ alkyl, C$_1$ to C$_6$ haloalkyl, C$_1$ to C$_6$ alkoxy and C$_1$ to C$_6$ alkylthio; C$_1$ to C$_6$ (alkyl) sulfonyl; benzene sulfonyl; substituted benzenesulfonyl wherein the benzene ring is substituted with from one to three substituents selected from the group consisting of halogen, nitro, cyano, C$_1$ to C$_6$ alkyl, C$_1$ to C$_6$ haloalkyl, C$_1$ to C$_6$ alkoxy and C$_1$ to C$_6$ alkylthio; an acyl group; and an inorganic or organic cation;

R$^4$ is selected from the group consisting of: C$_1$ to C$_6$ alkyl; C$_2$ to C$_6$ alkenyl; C$_2$ to C$_6$ haloalkenyl; C$_2$ to C$_6$ alkynyl; C$_2$ to C$_6$ haloalkynyl; substituted C$_1$ to C$_6$ alkyl wherein the alkyl group is substituted with a substituent selected from the group consisting of halogen, C$_1$ to C$_6$ alkoxy, C$_1$ to C$_6$ alkylthio, phenyl and substituted phenyl wherein the benzene ring is substituted with from one to three substituents selected from the group consisting of halogen, nitro, cyano, C$_1$ to C$_6$ alkyl, C$_1$ to C$_6$ haloalkyl, C$_1$ to C$_6$ alkoxy and C$_1$ to C$_6$ alkylthio;

R$^5$ is selected from the group consisting of: C$_1$ to C$_6$ alkyl; C$_1$ to C$_6$ fluoroalkyl; C$_2$ to C$_6$ alkenyl; C$_2$ to C$_6$ alkynyl; and phenyl; and n is an integer chosen from 2 to 5.

These compounds and their preparation are described in EP-A-Pat. No. 0080301.

A particularly preferred compound of formula (VII) is the compound of formula (VIII):

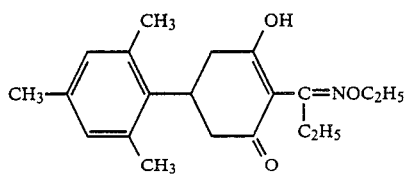

Further suitable herbicidal cyclohexane diones and their preparation are described and claimed in EP-B-No. 0085529. These compounds can be represented by formula (IX):

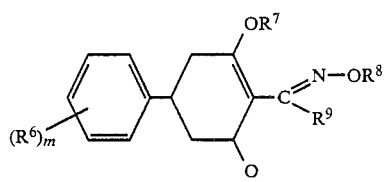

wherein
R$^6$, which may be the same or different, are selected from the group consisting of: halogen; nitro; cyano; C$_1$ to C$_6$ alkyl; C$_1$ to C$_6$ alkyl substituted with a substituent selected from the group consisting of halogen, nitro, hydroxy, C$_1$ to C$_6$ alkoxy and C$_1$ to C$_6$ alkylthio; C$_2$ to C$_6$ alkenyl; C$_2$ to C$_6$ alkynyl; hydroxy; C$_1$ to C$_6$ alkoxy; C$_1$ to C$_6$ alkoxy substituted with a substituent selected from halogen and C$_1$ to C$_6$ alkoxy; C$_1$ to C$_6$ alkenyloxy; C$_2$ to C$_6$ alkynyloxy; C$_2$ to C$_6$ alkanoyloxy; (C$_1$ to C$_6$ alkoxy)carbonyl; C$_1$ to C$_6$ alkylthio; C$_1$ to C$_6$ alkylsulfinyl; C$_1$ to C$_6$ alkylsulfonyl; sulfamoyl; N-(C$_1$ to C$_6$ alkyl)sulfamoyl; N,N-di(C$_1$ to C$_6$ alkyl)sulfamoyl; benzyloxy, substituted benzyloxy wherein the benzene ring is substituted with from one to three substituents selected from the group consisting of halogen, nitro, C$_1$ to C$_6$ alkyl, C$_1$ to C$_6$ alkoxy and C$_1$ to C$_6$ haloalkyl; the group NR$^9$R$^{10}$ wherein R$^9$ and R$^{10}$ are independently selected from the group consisting of hydrogen, C$_1$ to C$_6$ alkyl, C$_2$ to C$_6$ alkanoyl, benzoyl and benzyl; the groups formyl and C$_2$ to C$_6$ alkanoyl and the oxime, imine and Schiff base derivatives thereof; and at least one of X is not selected from the group consisting of halogen, C$_1$ to C$_6$ alkyl and C$_1$ to C$_6$ alkoxy;

R$^7$ is selected from the group consisting of: hydrogen; C$_1$ to C$_6$ alkyl; C$_2$ to C$_6$ alkenyl; C$_2$ to C$_6$ alkynyl; substituted C$_1$ to C$_6$ alkyl wherein the alkyl group is substituted with a substituent selected from the group consisting of C$_1$ to C$_6$ alkoxy, C$_1$ to C$_6$ alkylthio, phenyl and substituted phenyl wherein the benzene ring is substituted with from one to three substituents selected from the group consisting of halogen, nitro, cyano, C$_1$ to C$_6$ alkyl, C$_1$ to C$_6$ haloalkyl, C$_1$ to C$_6$ alkoxy and C$_1$ to C$_6$ alkylthio; C$_1$ to C$_6$ (alkyl) sulfonyl; benenesulfonyl; substituted benzenesulfonyl wherein the benzene ring is substituted with from one to three substituents selected from the group consisting of halogen, nitro, cyano, C$_1$ to C$_6$ alkyl, C$_1$ to C$_6$ haloalkyl, C$_1$ to C$_6$ alkoxy and C$_1$ to C$_6$ alkylthio; and acyl group; and an inorganic cation;

R$_8$ is selected from the group consisting of C$_1$ to C$_6$ alkyl; C$_2$ to C$_6$ alkenyl; C$_2$ to C$_6$ haloalkenyl; C$_2$ to C$_6$ alkynyl; C$_2$ to C$_6$ haloalkynyl; substituted C$_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;

$R_9$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl; and m is an integer chosen from 3 to 5.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the type of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 0.01% to 99% by weight of active ingredient.

The solid compositions may be in the form of dispersible or wettable powders, dusts, pellets, grains, and granules wherein the ingredients are mixed with a solid diluent. Powders and dusts may be prepared by mixing or grinding the ingredients with a solid carrier to give a finely divided composition. Granules, grains and pellets may be prepared by bonding the ingredients to a solid carrier, for example, by coating or impregnating the preformed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, powdered magnesia, magnesium oxide, magnesium sulfate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

The liquid compositions may comprise a solution or dispersion of the active ingredients in a liquid carrier containing one or more surfactant which act as wetting, emulsifying and/or dispersing agents. Examples of liquid carriers include: water; mineral oil fractions such as, for example kerosene, solvent naphtha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphthalenes; chlorinated hydrocarbons such as chlorobenzene and chlorotoluene; ketones such as, for example, cyclohexanone and isophorone; ethers such as anisole and strongly polar organic solvents such as, for example, dimethylformamide.

A preferred liquid composition comprises an aqueous suspension, dispersion or emulsion of the active ingredient which is suitable for application by spraying, atomizing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 5 to 99%, preferably 10 to 60%, by weight of active ingredient.

Emulsion or emulsifiable concentrates are conveniently prepared by dissolving the active ingredient in an organic solvent containing one or more surface active agents.

Pastes may be prepared by blending the finely divided active ingredient with a finely divided solid carrier, one or more surface active agents and optionally an oil. Oil dispersions may be prepared by grinding together the active ingredient, a hydrocarbon oil, and one or more surface active agents. Aqueous suspension concentrates may conveniently be prepared by bead milling a mixture of the active ingredient, water, at least one surface active agent and preferably at least one suspending agent. Suitable suspending agents include: hydrophilic colloids such as, for example, poly-(N-vinylpyrrolidone), sodium carboxymethylcellulose and the vegetable gums gum acacia and gum tragacanth; hydrated colloidal mineral silicates such as, for example, montmorillonite, beidellite, nontronite, hectorite, laponite, sauconite and bentonite; other cellulose derivatives; and poly (vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that certain cyclohexane dione herbicides are acidic. Therefore, these compounds may be formulated and applied as the salts of organic or inorganic bases.

In formulating and employing the cyclohexane dione compounds in the form of their salts either the salts per se, may be included in the formulation or the free acid may be used and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectare is suitable while from 0.01 to 5.0 kilograms per hectare may be preferred.

The compositions of the invention may comprise, in addition to one or more cyclohexane dione herbicides one or more compound which possess biological activity. For example, some cyclohexane dione herbicides are in general substantially more effective against mono-cotyledonous plants or grass species than against di-cotyledonous plants or broad-leaved species. As a result, in certain applications the herbicidal use of the compound of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Examples of useful complementary herbicides include:

A. benzo-2,1,3-thiadiazin-4-one-2,2-dioxides such as 3-isopropylbenzo-2,1,3-thiadiazin-4-one-2,2-dioxide (bentazon);
B. hormone herbicides, particularly the phenoxy alkanoic acids such as 4-chloro-2-methylphenoxy acetic acid (MCPA), 2-(2,4-dichlorophenoxy)propionic acid (dichlorprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy)propionic acid (mecoprop), and their derivatives (e.g. salts, esters and amides);
C. 3-[4-(4-halophenoxy)phenyl]-1,1-dialkylureas such as 3-[4-(4-chlorophenoxy)phenyl]-1,1-dimethylurea.
D. Dinitrophenols and their derivatives (e.g. acetates) such as 2-methyl-4,6-dinitrophenol (DNOC), 2-t-butyl-4,6-dinitrophenol (dinoterb), 2-secbutyl-4,6-dinitrophenol (dinoseb) and its ester, dinoseb acetate;
E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin) and 4-methylsulphonyl-2,6-dinitro-N,N-dipropylaniline (nitralin);
F. phenylurea herbicides such as N'-(3,4-dichlorophenyl)-N,N-dimethylurea (diuron) and N,N-dimethyl-N'-[3-(trifluoromethyl)phenyl]urea (flumeturon);
G. phenylcarbamoyloxyphenylcarbamates such as 3-[methoxycarbonylamino]phenyl (3-methylphenyl)-carbamate (phenmedipham) and 3-[ethoxycarbonylamino]phenyl phenylcarbamate (desmedipham);
H. 2-phenylpyridazin-3-ones such as 5-amino-4-chloro-2-phenylpyridazin-3-one (pyrazon);
I. uracil herbicides such as 3-cyclohexyl-5,6-trimethyleneuracil (lenacil), 5-bromo-3-sec-butyl-6-methyluracil (bromacil) and 3-t-butyl-5-chloro-6-methyluracil (terbacil);
J. triazine herbicides such as 2-chloro-4-ethylamino-6-(i-propylamino)-1,3,5-triazine (atrazine), 2-chloro-4,6-di(ethylamino)-1,3,5-triazine (simazine) and 2-azido-4-(i-propylamino)-6-methylthio-1,3,5-triazine (aziprotryne);
K. 1-alkoxy-1-alkyl-3-phenylurea herbicides such as 3-(3,4-dichlorophenyl)-1-methoxy-1-methylurea (linuron), 3-(4-chlorophenyl)-1-methoxy-1-methylurea (monolinuron) and 3-(4-bromo-4-chlorophenyl)-1-methoxy-1-methylurea (chlorobromuron).
L. thiolcarbamate herbicides such as S-propyl dipropylthiocarbamate (vernolate);
M. 1,2,4-triazin-5-one herbicides such as 4-amino-4,5-dihydro-3-methyl-6-phenyl-1,2,4-triazine-5-one (metamitron) and 4-amino-6-t-butyl-4,5-dihydro-3-methylthio-1,3,4-triazin-5-one (metribuzin);
N. benzoic acid herbicides such as 2,3,6-trichlorobenzoic acid (2,3,6-TBA), 3,6-dichloro-2-methoxybenzoic acid (dicamba) and 3-amino-2,5-dichlorobenzoic acid (chloramben);
O. anilide herbicides such as N-butoxymethyl-chloro-2',6'-diethylacetanilide (butachlor), the corresponding N-methoxy compound (alachlor), the corresponding N-i-propyl compound (propachlor) and 3',4'-dichloropropionanilide (propanil) 1 and 2-chloro-N-[pyrazol-1-ylmethyl]acet-2',6-xylidide (metazachlor);
P. dihalobenzonitrile herbicides such as 2,6-dichlorobenzonitrile (dichlobenil), 3,5-dibromo-4-hydroxybenzonitrile (bromoxynil) and 3,5-diiodo-4-hydroxybenzonitrile (ioxynil);
Q. haloalkanoic herbicides such as 2,2-dichlropropionic acid (dalapon), trichloroacetic acid (TCA) and salts thereof;
R. diphenylether herbicides such as 4-nitrophenyl 2-nitro-4-trifluoromethylphenyl ether (fluorodifen), methyl 5-(2,4-dichlorophenoxy)-2-nitrobenzoate (bifenox), 2-nitro-5-(2-chloro-4-trifluoromethylphenoxy)benzoic acid (acifluorfen) and salts and esters thereof, 2-chloro-4-trifluoromethylphenyl -b 3-ethoxy-4-nitrophenyl ether (oxyfluorfen) and 5-(2-chloro-4-(trifluoromethyl)phenoxy)-N-(methylsulfonyl)-2-nitrobenzamide (fomesafen); and
S. phenoxyphenoxypropionate herbicides such as 2-(4-(4'-trifluoromethylphenoxy)-phenoxy)-propionic acid methylester (trifop-methyl), 2-(4-((5-trifluoromethyl)-2-(pyridinyl)oxy)phenoxypropanoic acid (fluazifop) and esters thereof, 2-(4-((3-chloro-5-trifluoromethyl)-2-pyridinyl)oxy)phenoxy)propanoic acid (haloxyfop) and esters thereof, 2-(4-((6-chloro-2quinoxalinyl)oxy)phenoxypropanoic acid (xylofop) and esters thereof; and
T. sulfonyl urea herbicides such as 2-chloro-N-(4-methoxy-6-methyl-1,3,5-triazin-2-yl)-aminocarbonyl)benzenesulphonamide (chlorosulfuron), methyl 2-((((4,6-dimethyl-2-pyrimidinyl)amino)carbonyl)amino)sulphonylbenzoic acid (sulfometuron), 2-(((3-(4-methoxy-6-methyl-1,3,5-triazin-2-yl)carbonyl)amino)sulphonyl)benzoic acid (metsulfuron) and esters thereof;
U. imidazolidinone herbicides such as 2-(4,5-dihydro-4-isopropyl-4-methyl-5-oxoimidazol-2-yl)quinoline-3carboxylic acid (imazaquin), methyl 6-(4-isopropyl-4-methyl-5-oxo-2-imidazolin-2-yl)-m-toluate and p-toluate isomer (AC 222293)
V. arylanilide herbicides such as 1-methylethyl-N-benzoyl-N-(3-chloro-4-fluorophenyl)-L-alanine (flamprop-isopropyl), ethyl N-benzoyl-N-(3,4-dichlorophenyl)-DL-alaninate (benzoylprop-ethyl), N-(2,4-difluorophenyl)-2-(3-(trifluormethyl)phenoxy)-3-pyridinecarboxamide (diflufenican); and
W. amino acid herbicides such as N-(phosphonomethyl)glycine (glyphosate) and DL-homoalanin-4-yl(methyl)phosphinic acid (phosphinothricin) and their salts and esters; and X. organoarsenical herbicides such as monosodium methanearsonate (MSMA); and Y. miscellaneous herbicides including N,N-dimethyldiphenylacetamide (diphenamid), N-(1-naphthyl)phthalamic acid (naptalam) and 3-amino-1,2,4-triazole, 2-ethoxy-2,3-dihydro-3,3-dimethylbenzofuran methanesulfonate (ethofumesate), 1,4-epoxy-p-meth-2-yl 2-methylbenzyl ether (cinmethylin);

Z. Examples of useful contact herbicides include: bipyridylium herbicides such as those in which the ion (paraquat) and those in which the active entity is the 1,1'-ethylene-2,2'-dipyridylium ion (diquat);

The complementary herbicide is suitably present in the mixture or composition in an amount such that it is applied at its conventional rate.

The following Examples illustrate the invention.

In the examples the following references are used:

① Methyl capped nonyl phenol polyoxyethylene (N) (N=30 oxyethylene units) available from Speciality Chemicals Group, ICI PLC.

② Methyl capped $C_{12}-C_{13}$ alcohol polyoxethylene (N) (N<10 but >5 oxyethylene units) available from Speciality Chemicals Group, ICI PLC.

③ Methyl glycol laurate obtained by esterication of Methyl Ethoxyl (Trade Mark of ICI PLC) with lauric acid.

④ Polysiloxane - polyether copolymer obtainable from Th Goldschmidt AG under the Trade Name "Tegoplant WT10".

⑤ The solvent employed is trimethylbenzenes available as "Solvesso 100"

⑥ Sold as "Pluronic F38"

⑦ "Synperonic NPE 1800"

EXAMPLE 1

An emulsifiable concentrate of the type for use in conjunction with a tank mixed surfactant wetter was prepared as follows.

| | % w/v |
|---|---|
| Compound VIII | 10 |
| Methoxybenzene (anisole) | 40 |
| Sodium dioctylsulphosuccinate | 3 |
| Methyl capped nonyl phenol polyoxyethylene① | 2 |
| Solvent⑤ | to 100 |

The emulsifiable concentrate was stored for 1 month at 50° C. after which time it was determined that only 1.6% of Compound VIII had decomposed. In a similar composition in which methyl capped nonyl phenol polyoxyethylene was replaced with nonyl phenol polyoxyethylene per se, 9.5% of compound VIII had decomposed after a similar storage period.

EXAMPLE 2

This example illustrates various emulsifiable concentrate formulations which additionally include surfactant wetters.

| | | % w/v |
|---|---|---|
| (a) | Compound VIII | 10 |
| | Monochlorotoluenes | 40 |
| | Sodium dioctylsulphosuccinate | 3 |
| | Methyl capped nonyl phenol Polyoxyethylene① | 2 |
| | Nonyl phenol polyoxyethylene | 10 |
| | Solvent⑤ | to 100 |

-continued

| | | % w/v |
|---|---|---|
| (b) | Compound VIII | 10 |
| | Monochlorotoluenes | 40 |
| | Sodium dioctylsulphosuccinate | 3 |
| | Methyl capped nonyl phenol polyoxyethylene① | 2 |
| | Methyl capped $C_{12}-C_{13}$ polyoxyethylene② | 10 |
| | Solvent⑤ | to 100 |
| (c) | Compound VIII | 10 |
| | Monochlorotoluenes | 40 |
| | Sodium dioctylsulphosuccinate | 3 |
| | Methyl capped nonyl phenol polyoxyehtylene① | 2 |
| | Methyl glycol laurate③ | 10 |
| | Solvent⑤ | to 100 |
| (d) | Compound VIII | 10 |
| | Monochlorotoluenes | 40 |
| | Sodium dioctylsulphosuccinate | 3 |
| | methyl capped nonyl phenol polyoxyethylene① | 2 |
| | Methyl capped ethoxylated Silicone④ | 10 |
| | Solvent⑤ | to 100 |
| Comparative example | | |
| (e) | Compound VIII | 10 |
| | Monochlorotoluenes | 40 |
| | Nonyl phenol polyoxyethylene | 15 |
| | Solvent⑤ | to 100 |

The compositions of Example 2 were stored at 50° C. for 1 month after which time the percentage of compound VIII which had decomposed was assessed. The results are shown in Table 1.

TABLE I

| COMPOSITION | % COMPOUND VIII DECOMPOSED |
|---|---|
| 2a | 10.9 |
| 2b | 3.2 |
| 2c | 4.6 |
| 2d | 4.3 |
| 2e comparative | 14.0 |

EXAMPLE 3

Emulsifiable concentrates were prepared as follows:

| | | % w/v |
|---|---|---|
| (a) | Compound VIII | 10 |
| | nonyl phenol polyoxyethylene capped with chlorine ("Teric" '165) | 10 |
| | xylene | to 100 |
| Comparative example | | |
| (b) | Compound VIII | 10 |
| | nonyl phenol polyoxyethylene | 10 |
| | xylene | to 100 |

After one month storage at 50% the % decomposition of Compound VIII was 2.9% in composition 3a and 16.6% in comparative composition 3b.

EXAMPLE 4

Emulsifiable concentrates can also be prepared using the compounds of formula IX in particular those exemplified in EP-B-No. 0085529, for example as follows:

| | % w/v |
|---|---|
| 2-[1-(ethoxyimino)propyl]-3-hydroxy-5-(2,4,6-trimethyl-3-butyrylphenyl)cyclohex-2-enone | 12.5 |

|  | % w/v |
|---|---|
| methyl capped nonyl phenol polyoxyethylene[1] | 2 |
| sodium dioctysulphosuccinate | 3 |
| solvent[5] | to 100 |

EXAMPLE 5

The following emulsifiable concentrates were prepared using the herbicide 5-(3-acetyl-2,4,6-trimethylphenyl)-2-[1-ethoxyimino)propyl]-3-hydroxycyclohex-2en-1-one.

|  |  | % w/v |
|---|---|---|
| (a) | Herbicide | 12.5 |
|  | sodium dioctylsulphosuccinate | 3 |
|  | methyl capped nonyl phenol polyoxyethylene[1] | 2 |
|  | solvent ("Solvesso 200") | to 100 |
| Comparative Example | | |
| (b) | Herbicide | 12.5 |
|  | sodium dioctylsulphosuccinate | 1.5 |
|  | block copolymer of ethylene oxide and propylene oxide[6] | 3.5 |
|  | nonyl phenol ethylene oxide/-propylene oxide block copolymer | 1.0 |
|  | solvent ("Solvesso 200") | to 100 |

After 4 weeks at 50° C., 4.3% of the herbicide had discomposed in formulation of Example 5(a) and there was 7.3% decomposition in comparative Example 5(b). After 8 weeks at 50%, there was 10.3% and 14.6% decomposition of herbicide in Examples 5(a) and 5(b) respectively.

EXAMPLE 6

A further emulsifiable concentrate was prepared as follows:

|  | % w/v |
|---|---|
| Compound VIII | 10 |
| methyl capped nonyl phenol polyoxyethylene[1] | 2 |
| sodium dioctylsulphosuccinate | 3 |
| monochlorotoluene | 50 |
| methyl capped $C_{12}$-$C_{13}$ alcohol polyoxyethylene | 5 |
| solvent[5] | to 100. |

We claim:

1. A herbicidal composition comprising a herbicidal cyclohexane dione of the formula:

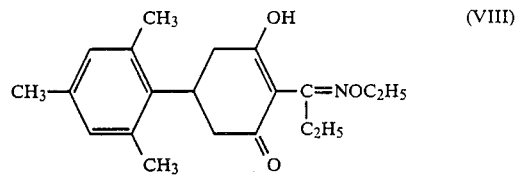

and a surfactant having terminal hydroxy groups in which the hydroxy groups have been replaced by blocking groups, said surfactant being methyl capped nonyl phenol polyoxyethylene having 30 oxyethylene units and/or methyl capped $C_{12}$-$C_{13}$ alcohol polyoxyethylene having <10 but >5 oxyethylene units, the surfactant stabilizing said dione against decomposition in the presence of water thereby improving the shelf-life of said composition.

2. In a method of controlling the growth of unwanted plants by applying to the plant or to the locus thereof a herbicidally effective amount of a herbicidal cyclohexane dione composition, the improvement which comprises using as said composition, a composition according to claim 1.

* * * * *